United States Patent
Suga et al.

(10) Patent No.: US 7,553,824 B2
(45) Date of Patent: Jun. 30, 2009

(54) KIT FOR DETERMINING POLYSACCHARIDE-BINDING ACTIVITY OF MONONUCLEAR CELLS PRESENT IN PERIPHERAL BLOOD

(75) Inventors: Tetsuya Suga, Chuo-ku (JP); Yasuyo Suga, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/117,999

(22) Filed: May 9, 2008

(65) Prior Publication Data

US 2008/0220452 A1 Sep. 11, 2008

Related U.S. Application Data

(60) Division of application No. 11/580,936, filed on Oct. 16, 2006, now Pat. No. 7,449,452, which is a continuation of application No. PCT/JP2005/007306, filed on Apr. 15, 2005.

(30) Foreign Application Priority Data

| Apr. 16, 2004 | (JP) | ............................. 2004-121616 |
| Aug. 10, 2004 | (JP) | ............................. 2004-233513 |
| Feb. 14, 2005 | (JP) | ............................. 2005-036312 |

(51) Int. Cl.
*A01N 43/04* (2006.01)

(52) U.S. Cl. .......................................... 514/54; 435/975

(58) Field of Classification Search .................... 514/54, 514/885; 435/7.24, 975
See application file for complete search history.

(56) References Cited

U.S. PATENT DOCUMENTS

| 5,106,616 | A | 4/1992 | McAnalley et al. |
| 5,705,398 | A * | 1/1998 | Mintz et al. ................. 435/501 |
| 6,956,120 | B2 | 10/2005 | Ikewaki et al. |
| 2001/0051717 | A1 * | 12/2001 | Wakshull et al. ....... 536/123.12 |
| 2004/0132131 | A1 * | 7/2004 | Markman et al. .......... 435/69.1 |
| 2006/0160766 | A1 | 7/2006 | Cheung |
| 2006/0188506 | A1 * | 8/2006 | Cheung ................... 424/155.1 |
| 2007/0031898 | A1 * | 2/2007 | Suga et al. ................. 435/7.21 |

FOREIGN PATENT DOCUMENTS

JP 04-024555 1/1992
JP 04-346791 12/1992

OTHER PUBLICATIONS

Oka M. et al., "In Vitro and in Vivo Analysis of Human Leukocyte Binding by the Antitumor Polysaccharide, Lentinan", Int. J. Immunopharmac., vol. 18, No. 3, pp. 211-216, (1996).
Suga T., et al., "Antitumor Activity of Lentinan in Murine Syngeneic and Autochthonous Hosts and Its Suppressive Effect on 3-Methylcholantherene-induced Carcinogenesis", Cancer Research, Nov. 1984, vol. 44, pp. 5132-5137.
50th Annual Mtg. Proc. Jpn., Cancer Assoc., 1991, pp. 259.
Vetvicka V., et al, "Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells", J. Clin Invest, Jul. 1996, vol. 98, No. 1, p. 50-61.
Brown G., et al., "Dectin-1 Is A Major β-Glucan Receptor On Macrophages", J. Exp. Med, Aug. 5, 2002, vol. 196, No. 3, pp. 407-412.
Daniel J. Allendorf, et al., "macrophages suttle orally administered beta-glucan to potentiate the CR3-dependent tumoricidal effects of monoclonal antibodies in mouse tumor models", Faseb Journal, FED. of American soc. for experimental biology, bethesda, MD, US, XP009099286, vol. 17, No. 7, May 10, 2003, p. C128.
Daniel J. Allendorf, et al. "Orally administered beta-glucan functions via anti-tumor mAbs and the complement system to recruit CR3+ neutrophils and macrophages that produce tumor regression and tumor-free survival", Molecular Immunology, Elmsford, NY, US, XP 009099285, vol. 40, No. 2-4, Sep. 6, 2003, pp. 195-196.
Penagiotis Kougias, et al., "Normal human fibroblasts express pattern recognition receptors for fungal (1->3)-beta-D-glucans", Infection and Immunity, XP002477857, vol. 69, No. 6, Jun. 2001, pp. 3933-3938.

* cited by examiner

*Primary Examiner*—Ralph Gitomer
(74) *Attorney, Agent, or Firm*—Oblon, Spivak, McClelland, Maier & Neustadt, P.C.

(57) ABSTRACT

A kit for the determination of the ability of a peripheral blood mononuclear cell to bind to a polysaccharide herein provided comprises a detection reagent comprising a fluorescence-labeled immunostimulant polysaccharide; and a reference reagent comprising a fluorescence-labeled material of a polysaccharide different from that used in the fluorescence-labeled immunostimulant polysaccharide, and/or an immunostimulant polysaccharide which is not labeled with any fluorescent material and whose polysaccharide moiety is identical to that included in the fluorescence-labeled immunostimulant polysaccharide. The use of this kit would permit the estimation of the polysaccharide-binding ability of a peripheral blood mononuclear cell in a higher precision of estimation.

19 Claims, 5 Drawing Sheets

ICR whole-%MC

ICR whole-%GC

KIT FOR DETERMINING POLYSACCHARIDE-BINDING ACTIVITY OF MONONUCLEAR CELLS PRESENT IN PERIPHERAL BLOOD

CROSS REFERENCES TO RELATED APPLICATIONS

This application is a divisional application of 11/580,936 filed Oct. 16, 2006, now U.S. Pat. No. 7,449,452, which is continuation of International Patent Application No. PCT/JP05/007306, filed on Apr. 15, 2005, and claims priority to Japanese Patent Application No. 121616/2004, filed on Apr. 16, 2004, Japanese Patent Application No. 233513/2004, filed on Aug. 10, 2004, and Japanese Patent Application No. 036312/2005, filed on Feb. 14, 2005, all of which are incorporated herein by reference in their entireties.

BACKGROUND OF THE INVENTION

1. Technical Field

The present invention relates to a kit effectively used for easily determining or judging on whether a specific immunostimulant polysaccharide is effective, or not, for a specific subject as an immunostimulant agent and a method for estimating the efficiency of a candidate material as an immunostimulant agent.

2. Background of the Invention

It has commonly been known that the immunostimulant polysaccharides such as β-glucans represented by lentinan are effective as immunostimulant agents and/or anti-pernicious tumor agents, but it has likewise been known that the development of their effect would greatly be affected by the variations between individuals (Non-Patent Document No. 1 specified later).

On the other hand, it has been known that the immunostimulant polysaccharides are bonded to the mononuclear cells such as monocytes, granulocytes and lymphocytes, which are present in the peripheral blood of the mammals such as human beings and mice, on the surface of these mononuclear cells (Non-Patent Document Nos. 2 and 3 specified later). Moreover, it has also been proved that the ability of the immunostimulant polysaccharide to bind to mononuclear cells present in the peripheral blood would variously be affected by the differences between individuals or the differences between mouse strains and accordingly, there would be a high possibility such that the binding ability of the immunostimulant polysaccharide may correlate with the development of the foregoing effects of the polysaccharide.

As means for estimating or determining the ability of the immunostimulant polysaccharide to bind to mononuclear cells present in the peripheral blood (peripheral blood mononuclear cell(s)), there has been known, for instance, a method which makes use of an antibody against an immunostimulant polysaccharide such as anti-lentinan antibody. However, this method suffers from various problems in that it is difficult to use such an anti-lentinan antibody in this method since the antibody is an IgM and that the anti-lentinan antibody is a self-productive antibody and accordingly, it would be quite difficult to constantly supply such an antibody having a uniform titer. In addition, the method further suffers from a problem such that the method requires the use of complicated operations since the method requires the step of separating the white blood cells fraction from the blood and the subsequent step for subjecting the antibody to a reaction in the presence of the blood serum.

Contrary to this, there has also been known a method in which a fluorescence-labeled immunostimulant polysaccharide is added to peripheral blood mononuclear cells (whole blood), followed by cultivating the same and the subsequent determination of the fluorescent intensity emitted therefrom (see Non-Patent Document Nos. 4 and 5).

This method is one which permits the considerably efficient and highly precise determination of the ability of a labeled immunostimulant polysaccharide to bind to peripheral blood mononuclear cells as compared with the foregoing method which makes use of, for instance, an anti-lentinan antibody. As a result of the examinations carried out by the inventors of this invention, however, the values measured by the method each include not only the linkages specific to or peculiar to the immunostimulant polysaccharide, but also the linkages non-specific thereto. Accordingly, even if the method provides a positive result, the positive value does not always correspond to only the binding ability specific to the immunostimulant polysaccharide derived from a subject to be examined and therefore, it has been proved that the binding ability of the subject examined may not necessarily correlate with the desired effect.

Non-Patent Document No. 1: Cancer Res., 1984, 44:5132;
Non-Patent Document No. 2: $50^{th}$ Annual Mtg. Proc. Jpn. Cancer Assoc., p. 259 (1991);
Non-Patent Document No. 3: Int. J. Immunopharmac., 1996, 18:211;
Non-Patent Document No. 4: J. Clin. Invest., Vol. 98, No. 1, July 1996, pp. 50-61;
Non-Patent Document No. 5: J. Exp. Med., Vol. 196, No. 3, Aug. 5, 2002, pp. 407-412.

SUMMARY OF THE INVENTION

It is an object of the present invention to provide a kit for the determination of the ability of the peripheral blood mononuclear cells to bind to a polysaccharide, which permits the prediction of the foregoing ability with a quite high precision.

It is another object of the present invention to provide a method for judging the efficiency of an immunostimulant polysaccharide as an immunostimulant agent with a higher or more improved precision.

The present invention has been developed on the basis of the finding that the efficiency of an immunostimulant polysaccharide as an immunostimulant agent can be estimated with a higher precision, in addition to the use of a detection reagent comprising a fluorescence-labeled immunostimulant polysaccharide, by the use of a reference reagent which comprises a fluorescence-labeled material of a polysaccharide different from that included in the fluorescence-labeled immunostimulant polysaccharide, or a reference reagent which comprises an immunostimulant polysaccharide which is not labeled with any fluorescent material and whose polysaccharide moiety is identical to that included in the fluorescence-labeled immunostimulant polysaccharide used in the detection reagent and that this method would permit the effective solution of the foregoing problems.

In other words, the present invention herein provides a kit for the determination of the ability of the peripheral blood mononuclear cells to bind to a polysaccharide, which comprises a detection reagent comprising a fluorescence-labeled immunostimulant polysaccharide; and a reference reagent which comprises a fluorescence-labeled material of a polysaccharide different from that used in the fluorescence-labeled immunostimulant polysaccharide, or a reference reagent comprising an immunostimulant polysaccharide which is not labeled with any fluorescent material and whose polysaccharide moiety is identical to that included in the fluorescence-labeled immunostimulant polysaccharide.

The present invention also provides a method for estimating the efficiency of an immunostimulant polysaccharide as an immunostimulant agent, which comprises the following steps:

bringing a sample blood to be tested into contact with a detection reagent comprising a fluorescence-labeled immunostimulant polysaccharide to thus obtain a fraction containing target peripheral blood mononuclear cells in the blood, and measuring the fluorescent intensity of the fraction to thus determine the amount (B) of the target peripheral blood mononuclear cells bonded to the fluorescence-labeled immunostimulant polysaccharide;

bringing the sample blood into contact with a reference reagent containing a fluorescence-labeled material of a polysaccharide different from that included in the fluorescence-labeled immunostimulant polysaccharide used in the detection reagent to thus give a target peripheral blood mononuclear cell-containing fraction of the sample blood, and measuring the fluorescent intensity of the fraction to thus determine the amount (A) of the target peripheral blood mononuclear cells bonded to the fluorescence-labeled material of the different polysaccharide, provided that this step can be omitted when the sample blood is brought into contact with a detection reagent which simultaneously comprises a un-labeled material of the polysaccharide included in the reference reagent or the polysaccharide labeled with another fluorescent dye; and calculating the difference (B−A) between the amounts (A) and (B) of the target peripheral blood mononuclear cells bonded to the polysaccharides to thus examine on whether, or not, the immunostimulant polysaccharide used is effective for the immuno-augmentation of the mammal from which the blood sample is collected.

According to the present invention, there is also provided a method for estimating the efficiency of an immunostimulant polysaccharide as an immunostimulant agent, which comprises the following steps:

bringing a sample blood to be tested into contact with a detection reagent comprising a fluorescence-labeled immunostimulant polysaccharide to thus obtain a target peripheral blood mononuclear cell-containing fraction of the sample blood, and measuring the fluorescent intensity of the fraction to thus determine the amount (B) of the target peripheral blood mononuclear cells bonded to the fluorescence-labeled immunostimulant polysaccharide;

bringing the sample blood into contact with a reference reagent containing an immunostimulant polysaccharide which is not labeled with any fluorescent material and whose polysaccharide moiety is identical to that included in the fluorescence-labeled immunostimulant polysaccharide used in the detection reagent, and the detection reagent comprising the fluorescence-labeled immunostimulant polysaccharide to thus give a target peripheral blood mononuclear cell-containing fraction of the sample blood, and measuring the intensity of the fraction to thus determine the amount (A) of the target peripheral blood mononuclear cells bonded to the fluorescence-labeled immunostimulant polysaccharide; and judging on whether, or not, the immunostimulant polysaccharide used is effective for the immuno-augmentation of the mammal from which the blood sample is collected, on the basis of the measured value (A) and the difference (B−A) between the amounts (A) and (B) of the mononuclear cells bonded to the polysaccharides.

BRIEF DESCRIPTION OF THE DRAWINGS

FIG. 8A represents the results obtained using 20 μg/mL of fluorescein-labeled lentinan; FIG. 8B represents the results obtained using 5 μg/mL of fluorescein-labeled lentinan; FIG. 8C represents the results obtained using 20 μg/mL of FITC-labeled dextran. *: $p<0.05$; ***: $p<0.001$ (Comparison between two groups: Student's T test). In FIG. 8, FL represents fluorescein-labeled lentinan; FD represents FITC-labeled dextran; LNT represents un-labeled lentinan; +L means that the tests are carried out in the coexistence of fluorescein-labeled lentinan and un-labeled lentinan; and each numerical value is expressed in terms of the concentration (unit: μg/mL).

DETAILED DESCRIPTION OF THE PREFERRED EMBODIMENTS

Figure 1:
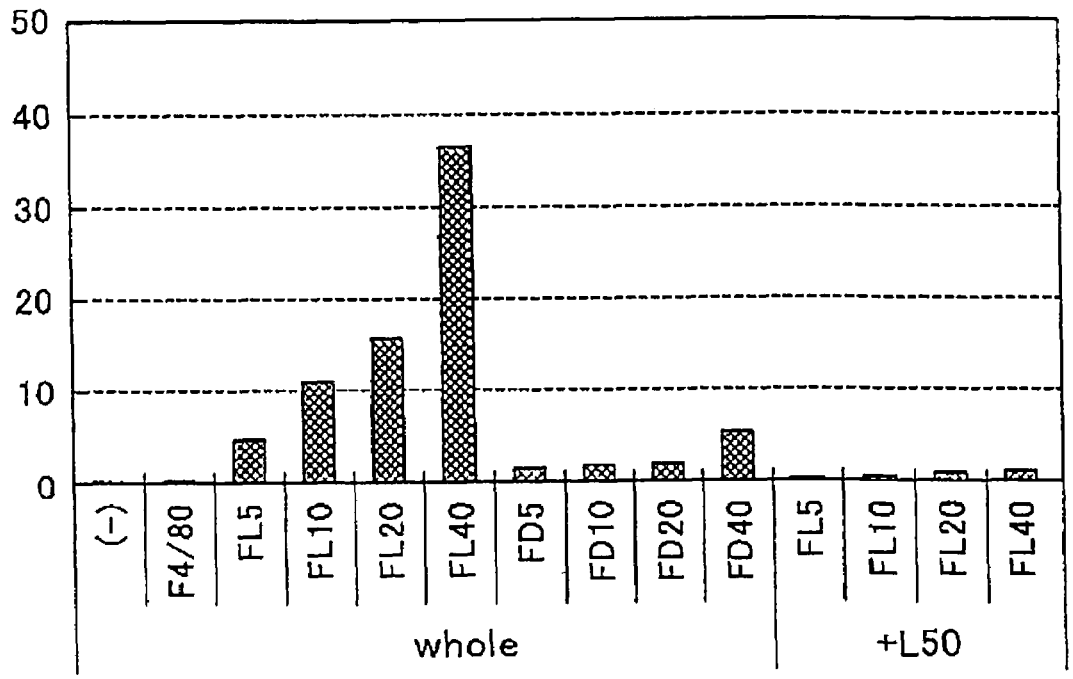
FIG. 1 shows the results of the fluorescein-labeled lentinan-binding to monocytes tests, the FITC-labeled dextran-binding to monocytes tests, and the binding to monocytes test simultaneously using fluorescein-labeled lentinan and un-labeled lentinan.

The polysaccharide moiety of the fluorescence-labeled immunostimulant polysaccharide used in the present invention may be any one, inasmuch as a reactive group such as —CHO, —COOH, —NH$_2$, —NHS, —CN or an epoxy group can be introduced into the glucose residue of the polysaccharide moiety. Examples thereof include β-glucans, α-glucans, hetero-polysaccharides (preferably hetero-glucans) and protein-bound glucans. Preferably used herein include β-glucans and more preferably lentinan, zymosan, pachymaran, schizophyllan, pustulan, scleroglucan and lichenan. In respect of these polysaccharides, the molecular weight thereof is not restricted to any specific range at all.

Examples of the fluorescent materials herein used for introducing fluorescence-labels into the foregoing polysaccharides are those carrying reactive groups such as $NH_2$—, COOH— and/or imide groups in the molecules (including fluorometrically detectable substances by using a secondary fluorescent material such as fluorescence-labeled avidin, for instance, biotin) (see, for instance, New Experimental Courses III of Biochemistry, Glucide I (Vol. 1), infra p. 19, and infra p. 95 (1990), published by Tokyo Kagaku Dojin Publishing Company; ibid, Glucide I (Vol. 2), infra p. 605, and infra p. 743; ibid, Glucide II, infra p. 283). Preferably used herein include, for instance, fluorescent materials and/or biotin compounds having —$NH_2$ (including imide) group(s). The colors of the fluorescent materials are not restricted to specific ones, but they can desirably emit fluorescent light rays having wavelengths capable of being detected by the flow cytometrical analysis such as FACS. Preferred are, for instance, fluorescein type compounds. Specific examples thereof are fluorescein 5-thiosemicarbazide and FITC (fluorescein isothiocyanate).

The fluorescence-labeled material of a polysaccharide different from that included in the fluorescence-labeled immunostimulant polysaccharide used in the detection reagent, which is a component of the reference reagent used herein, may be any fluorescence-labeled material of a polysaccharide capable of forming linkages with the peripheral blood mononuclear cells through a manner different from that through which the fluorescence-labeled immunostimulant polysaccharide used in the detection reagent forms linkages with the mononuclear cells, wherein the polysaccharide is fluorometrically labeled with the same fluorescent dye used for labeling the immunostimulant polysaccharide used in the detection reagent. For instance, the reference reagent used when estimating the ability of $\beta$-1,3-glucan to form linkages with the mononuclear cells may be $\alpha$-glucan and hetero-polysaccharides (preferably hetero-glucans), which are fluorometrically labeled with the same fluorescent dyes used for labeling $\beta$-glucan. The molecular weight thereof is not restricted to any specific range and the polysaccharide may be a monosaccharide or a disaccharide, but the molecular weight thereof is suitably 0.01 to 100 times (preferably 0.1 to 10 times and more preferably approximately identical to) that of the target polysaccharide to be evaluated. The fluorescent intensity should be 0.01 to 100 times (preferably 0.1 to 10 times and more preferably approximately identical to) that of the target fluorescence-labeled polysaccharide (used in the detection reagent) to be evaluated, when expressing it in terms of the reduced intensity per glucose.

In the present invention, it is also possible to use for reference an immunostimulant polysaccharide which is not labeled with any fluorescent material and whose polysaccharide moiety is identical to that included in the fluorescence-labeled immunostimulant polysaccharide used in the detection reagent.

In the present invention, the both detection and reference reagents are preferably liquid and accommodated in separate containers, respectively. In this case, each aqueous solution contains a detection or reference reagent in an amount ranging from 1 to 10,000 μg/mL (preferably 10 to 1,000 μg/mL and more preferably 100 to 500 μg/mL) and it may likewise comprise an appropriate antiseptic (such as sodium azide) and/or an agent for inhibiting the flow ability of the cytoplasmic membrane (such as sodium azide or cytochalasin B).

Preferably, the kit according to the present invention is further combined with a hemolysis/fixation liquid, a washing/analysis liquid and/or a blood-collection tube.

The material for such a blood-collection tube is not limited to any particular one, but the blood-collection tube may be one made of, for instance, glass, polyethylene, polypropylene or polystyrene and preferably used herein are those subjected to an anti-coagulation treatment with, for instance, heparin, citric acid or EDTA. The blood-collection capacity thereof is preferably 0.01 to 10 mL and particularly preferably 1 to 5 mL.

In the present invention, the blood is collected in the blood-collection tube, the collected blood is then blended with a reference reagent-containing liquid (Liquid A) (the addition thereof can be omitted when the detection reagent simultaneously comprises a un-labeled material of the polysaccharide different from that included in the fluorescence-labeled immunostimulant polysaccharide or a polysaccharide material labeled with another fluorescent dye) or a detection reagent-containing liquid (Liquid B) in a ratio by volume ranging from 1/100 to 1/2 (preferably 1/10 to 1/20) (in this respect, the final concentration of the polysaccharide component ranges from 0.1 to 1,000 μg/mL, preferably 1 to 100 μg/mL, more preferably 10 to 50 μg/mL) and the resulting mixture is allowed to stand for a time ranging from 5 to 180 minutes (preferably 15 to 90 minutes and more preferably 30 to 60 minutes). The temperature during this step preferably falls within the range of from 0 to 50° C.

Moreover, this operation can likewise be carried out after the completion of the treatment with a hemolysis/fixation liquid as will be described below.

The hemolysis/fixation liquid may be a hypotonic liquid such as water, which can hemolyze blood cells. For instance, usable herein include hemolytic solutions such as those containing ammonium chloride and commercially available solutions (such as FACS Lysing Solution (available from BD Company)). The amount thereof to be added ranges from 1 to 100 times (preferably 2 to 50 times and more preferably 10 to 40 times) that of the blood sample solution to be treated. More specifically, the hemolysis/fixation liquid is blended with the blood in such an amount, followed by allowing the resulting mixture to stand at a temperature ranging from 0 to 40° C. (preferably room temperature) for a time ranging from 1 to 60 minutes (preferably 5 to 30 minutes and more preferably 10 to 15 minutes) to thus hemolyze the blood cells, the subsequent centrifugation and the removal of the resulting supernatant. In this connection, when it takes not less than 24 hours till the measurement is initiated, it is desirable that the cells are fixed. In such a case, for instance, the blood cells are fixed using a solution (such as FIX & PERM Reagent A available from Caltag Company) to which a formalin-containing fixing agent (such as formaldehyde) is added according to the procedures similar to those used above, followed by the centrifugation of the resulting mixture, the removal of the resulting supernatant, if desired, the washing of the residue with a washing/analysis liquid, then allowing the same to stand at a temperature ranging from 0 to room temperature (preferably storage thereof in a refrigerator) and the inspection or determination of the stored residue within 72 hours (preferably within 48 hours).

The washing/analysis liquid used herein may be, for instance, a isotonic solution or liquid such as physiological saline and examples thereof are commercially available reagents such as PBS (phosphate buffered saline) type ones. These washing/analysis liquid may, if necessary, comprise BSA (bovine serum albumin), sodium azide and/or ethylene glycol (for instance, such as a washing buffer (PBS(−)+0.1% BSA+0.1% sodium azide)). The amount thereof to be added ranges from 0.5 to 10 times (preferably 1 to 4 times) that of the blood to be treated. More specifically, it is preferred that the washing/analysis liquid is blended with the blood in such an amount, followed by the centrifugation of the resulting mixture and the subsequent removal of the resulting supernatant.

These operations are repeated one to several times, then the washing/analysis liquid is again added to the resulting residue in an amount ranging from 0.5 to 10 times (preferably 1 to 4 times) that of the blood to be treated, followed by mixing them and the analysis thereof according to the flow cytometry technique. In this respect, when it takes not less than 24 hours till the measurement is initiated, it is desirable to use a washing/analysis liquid which comprises an antiseptic and/or an agent for inhibiting the flow ability of the cytoplasmic membrane (such as sodium azide or cytochalasin B).

The blood used in the kit according to the present invention may be one immediately after the collection thereof, one stored in, for instance, an ice or a refrigerator within a short period of time or one stored in a frozen condition at a temperature of not higher than $-30°$ C. In this respect, the blood sample stored in a frozen condition is used after thawing the same by the usual method, upon the practical use thereof.

The kit of the present invention can be applied to the staining of not only the mononuclear cells present in the blood, but also other cell suspensions. More specifically, the kit of the present invention can be applied to the staining of the suspensions containing a variety of cell strains (such as cancer cell strains and/or leukocyte cell strains), and cell-suspending liquids (cell suspensions) containing cancer tissues or various kinds of organs (such as lymph node (Example), spleen, lung, liver, enteron and skin) (which may likewise include suspensions of single cells obtained by treating these cell suspensions with EDTA or an enzyme (such as trypsin or collagenase)). The measurements can be carried out according to the foregoing operations insofar as the single cell suspension is prepared in such a manner that the cell density of the resulting suspension falls within the range of from $1\times10^3$ to $10^8$ cells/mL (preferably $1\times10^4$ to $10^7$ cells/mL and more preferably $1\times10^5$ to $10^6$ cells/mL).

Moreover, the kit according to the present invention can be applied not only to single color analyses, but also to multi-color analyses. More specifically, the analysis of the binding ability can be carried out while combining it with the flow cytometry which makes use of an antibody against, for instance, a specific substance present on the exterior or interior of a certain cell (such as a surface antigen) or an intracellular substance (such as cytokines). In this case, for instance, when analyzing a substance present on the cell surface, the measurement can easily be carried out by the simultaneous use of the antibody against a cell surface substance in the reference reagent-containing liquid or the detection reagent-containing liquid to be applied to the blood-collection tube, during the operation which is performed while the liquid is added to the blood-collection tube. It would be simpler to use an antibody labeled with a fluorescence-labeling substance other than that used in Liquid A and/or Liquid B. It is also possible to use an antibody labeled with, for instance, biotin and to treat with avidin labeled with another fluorescence-labeling substance after washing. In addition, when using a label-free antibody, it is also possible to carry out the desired measurements using a secondary antibody against the label-free antibody (using an antibody labeled with a fluorescence-labeling substance different from those used in Liquid A and/or Liquid B or an antibody labeled with, for instance, biotin, and then treating with avidin labeled with another fluorescence-labeling substance after washing). It is also possible to carry out the measurements by the treatment with an antibody after the hemolysis operation, without the coexistence of any antibody during the operation which is performed while the reference reagent-containing liquid or the detection reagent-containing liquid is added to the blood-collection tube.

Moreover, when measuring an intracellular substance, the measurement can be carried out by subjecting to a permealizing treatment using a cell membrane-permeating buffer (such as FIX & PERM Reagent B available from Caltag Company) and then treating with an antibody, after the completion of the hemolysis/fixation operations.

As has been described above, the present invention herein provides the method comprising the following steps:

A step for bringing the blood sample to be tested into contact with a detection reagent comprising a fluorescence-labeled immunostimulant polysaccharide to thus obtain a fraction containing target peripheral blood mononuclear cells present in the blood, and measuring the fluorescent intensity of the fraction to thus determine the amount (B) of the target peripheral blood mononuclear cells bonded to the fluorescence-labeled immunostimulant polysaccharide;

A step for bringing the blood sample into contact with a reference reagent containing a fluorescence-labeled material of a polysaccharide different from that used in the fluorescence-labeled immunostimulant polysaccharide included in the detection reagent to thus give a target peripheral blood mononuclear cell-containing fraction of the sample blood, and measuring the fluorescent intensity of the fraction to thus determine the amount (A) of the target peripheral blood mononuclear cells bonded to the fluorescence-labeled material (provided that this step can be omitted when using a detection reagent which simultaneously comprises a un-labeled material of a polysaccharide different from that included in the fluorescence-labeled immunostimulant polysaccharide or the polysaccharide labeled with another fluorescent dye); and A step for calculating the difference (B−A) between the amounts (A) and (B) of the mononuclear cells bonded to the polysaccharides to thus judge on whether, or not, the immunostimulant polysaccharide used is effective for the immuno-augmentation of the mammal from which the blood sample is collected. In this connection, the amount of the linked body or the linked amount can be expressed in terms of the number (or the rate) of linked cells (those appearing in the following description are shown in the same way also).

Moreover, when using a reference reagent which comprises an immunostimulant polysaccharide which is not labeled with any fluorescent material and whose polysaccharide moiety which is identical to that included in the immunostimulant polysaccharide used in the detection reagent, the method comprises the following steps:

A step for bringing a sample blood to be tested into contact with a detection reagent comprising a fluorescence-labeled immunostimulant polysaccharide to thus obtain a target peripheral blood mononuclear cell-containing fraction of the sample blood, and measuring the fluorescent intensity of the fraction to thus determine the amount (B) of the target peripheral blood mononuclear cells bonded to the fluorescence-labeled immunostimulant polysaccharide; and A step for bringing the sample blood into contact with a reference reagent containing the same immunostimulant polysaccharide which is not labeled with any fluorescent material, and the detection reagent comprising the fluorescence-labeled immunostimulant polysaccharide to thus give a target peripheral blood mononuclear cell-containing fraction of the sample blood, and measuring the fluorescent intensity of the fraction to thus determine the amount (A) of the target peripheral blood mononuclear cells bonded to the fluorescence-labeled immunostimulant polysaccharide.

Accordingly, the method would permit the judgment on whether, or not, the immunostimulant polysaccharide used is effective for the immuno-augmentation of the mammal from which the blood sample is collected on the basis of the measured value (A) and the difference (B−A) between the amounts (A) and (B) of the mononuclear cells bonded to the polysaccharides.

Thus, the present invention permits the elimination of the amount of the non-specifically linked polysaccharides and accordingly, the invention permits the determination of only the amount of the target immunostimulant polysaccharides or the specifically linked immunostimulant polysaccharides. Moreover, the simultaneous use of the foregoing two estimation methods would permit the elimination of the amount of the non-specifically linked anti-tumor polysaccharides and the use of the fluorescence-labeling of an immunostimulant polysaccharide would permit the confirmation of whether the manner of the linkage of the polysaccharide with the mononuclear cells is changed or not, likewise permit the determination of only the amount of the polysaccharides used which are specifically bonded to the mononuclear cells and accordingly, the present invention permits the highly precise estimation of the effectiveness of the immunostimulant polysaccharide as an immunostimulant agent.

According to the present invention, when using, in addition to the use of a detection reagent comprising a fluorescence-labeled immunostimulant polysaccharide, a reference reagent comprising a fluorescence-labeled material of a polysaccharide different from that used in the fluorescence-labeled immunostimulant polysaccharide (the use of such reference reagent would permit the determination of the amount of non-specifically linked different polysaccharides), or incorporating un-labeled material of a different polysaccharide or a labeled material thereof with another fluorescent dye into the detection reagent, it is possible to eliminate the amount of any non-specifically linked different polysaccharides from the previously measured result and thus one can determine the ability of the target immunostimulant polysaccharide to bind with the mononuclear cells. Therefore, the present invention has such an advantage that it can highly precisely evaluate the effectiveness of the immunostimulant polysaccharide as an immunostimulant agent.

On the other hand, when using, in addition to the use of a detection reagent comprising a fluorescence-labeled immunostimulant polysaccharide, a reference reagent comprising the same immunostimulant polysaccharide which is not labeled with any fluorescent material, the fluorescence-labeling of the immunostimulant polysaccharide would permit the confirmation of whether the manner of the linkage of the polysaccharide with the mononuclear cells is not changed at all, likewise permit the precise determination of only the ability of the target immunostimulant polysaccharide per se to bind to the cells and accordingly, the present invention permits the highly precise estimation of the effectiveness of the immunostimulant polysaccharide as an immunostimulant agent.

Consequently, when using, in addition to the use of a detection reagent comprising a fluorescence-labeled immunostimulant polysaccharide, a first reference reagent comprising a fluorescence-labeled material of a polysaccharide different from that used in the fluorescence-labeled immunostimulant polysaccharide (the use of the first reference reagent can be omitted, when the detection reagent simultaneously comprises an un-labeled material of a different polysaccharide or a fluorescence-labeled material of the polysaccharide labeled with another fluorescent dye), and a second reference reagent comprising the same immunostimulant polysaccharide free of any fluorescence-label, it is possible to further precisely determine the ability of the target immunostimulant polysaccharide per se to bind with the mononuclear cells and therefore, the present invention thus permits the considerably precise estimation of the effectiveness of the immunostimulant polysaccharide as an immunostimulant agent.

In addition, the kit of the present invention may comprise a detection reagent, a reference reagent, a hemolysis/fixation liquid, a washing/analysis liquid and a blood-collection tube in combination and it permits the rapid and simple determination of any discrepancy (or difference) in fluorescent intensity and the ability of cells derived from individuals to specifically bind to immunostimulant polysaccharides.

Then the present invention will now be described below in detail with reference to the following Examples.

EXAMPLES

Example 1

Method for the Preparation of Fluorescein-Labeled Lentinan

Lentinan (a product available from Ajinomoto Co., Ltd.) was dispersed in distilled water, while kneading the same in a mortal and lentinan was dissolved by treating the resulting dispersion in an autoclave maintained at 120° C. for 20 minutes to thus obtain a solution used in the following steps.

The solution of lentinan (4 mg/mL) was mixed with the same volume of a 4 mM sodium metaperiodate solution and then the resulting mixture was stirred at 4° C. over a whole day and night (reactive groups: —CHO were introduced through an oxidative cleavage reaction). Then ethylene glycol was added to the reaction system in an amount of 1/60 time the whole volume of the system to thus inactivate the metaperiodic acid present therein and then the resulting reaction system was dialyzed against distilled water at 4° C. over a whole day and night. To the liquid thus recovered, there was added a 200 μg/mL solution of fluorescein 5-thiosemicarbazide (a product available from Molecular Probes Company) in an amount of ½ time the initial volume of the lentinan solution and the pH value of the mixture was adjusted to 9.5 with an NaOH solution, followed by the stirring of the mixture at 4° C. over a whole day and night under the light-shielding conditions to thus label lentinan with fluorescent material. After the completion of the reaction, a 5 mg/mL sodium borohydride solution was added to the reaction system in an amount of 1/12.5 time the initial volume of the lentinan solution, followed by the stirring of the mixture at 4° C. over a whole day and night under the light-shielding conditions (for the reduction of Schiff bases and the conversion of the aldehyde into an alcohol). Finally, the pH of the system was adjusted to 7.0 with an HCl solution and then the system was dialyzed against distilled water at 4° C. over at least a whole day and night under the light-shielding conditions. After the completion of the dialysis, the liquid was recovered, followed by the addition of sodium azide to a final concentration of 0.02% and the subsequent storage thereof in a refrigerator under the light-shielding conditions.

Method for the Determination of the Binding Ability Using Whole Blood

The blood was collected through the heart of ICR mice (5 to 8-week-old female mice purchased from CLEA Japan, inc.) under the anesthetization with ether using heparin-containing syringes. The heparin-treated blood was dispensed into Falcon 2054 tubes in an amount of 90 μL/tube under ice-cooled conditions and the fluorescein-labeled lentinan was likewise dispensed into these tubes in an amount of 10

μL/tube. After the elapse of not less than 30 minutes, there was added, to each tube, 3 μL/tube of a PE (phycoerythrin)-labeled antibody against the surface antigen F4/80 of the mouse monocyte (PE-labeled anti-mouse F4/80 antibody available from Serotec Company). Further, after the elapse of an additional time on the order of not less than 30 minutes, there was added, to each tube, 3 mL/tube of FACS Lysing Solution (a hemolysis/fixation liquid available from BD Company; diluted 10 times with distilled water) and then the resulting mixture was allowed to stand at room temperature for 10 minutes for the hemolysis of the blood sample. After the centrifugation at 1500 rpm and 4° C. for 5 minutes, the resulting residues were washed with 1 mL of a washing buffer (PBS(−)+0.1% BSA+0.1% sodium azide) (washing/analysis liquid), suspended in 0.5 mL of the washing buffer, passed through a mesh and then subjected to the 2-color (fluorescein/PE) analysis using FACS Calibur.

We established gates for monocytes (MC), granulocytes (GC) and lymphocytes (LC) on the basis of forward and side scatter, and for analysis of monocytes, developed on Fluorescein/PE to thus determine the rate of the fluorescein-positive cells among the PE-positive cells, and for analysis of granulocytes and lymphocytes, determined the rate of the fluorescein-positive cells (the results thus obtained are shown in, for instance, FIG. 1 (indicated by FL)).

The similar analysis was carried out using FITC-labeled dextran (having a molecular weight of 2,000,000 available from Sigma Company) as a control (reference reagent 1) for the fluorescein-labeled lentinan (the results thus obtained are shown in, for instance, FIG. 1 (FD)).

Test on Binding-Inhibitory Effect of Lentinan

Upon the determination of the binding ability and prior to the dispensation of the whole blood into tubes, a 2 mg/mL lentinan solution diluted 10 times with PBS(−) was introduced into each tube in an amount of 25 μL/tube while ice-cooling the tubes, then the whole blood was dispensed into the tubes in an amount of 65 μL/tube and thereafter, a solution of fluorescein-labeled lentinan was added to each tube in an amount of 10 μL/tube (the final concentration of the lentinan solution for inhibition was set at 50 μg/mL). Then the subsequent operations were carried out according to the same procedures used above in the method for determining the binding ability (the previous section). (The results thus obtained are shown in FIG. 1 (indicated by FL+L50)).

Test Carried out Using Blood Stored in Frozen Conditions

Binding-inhibitory tests were carried out using the blood which had been collected from Lewis rats (9 to 10-week-old male rats purchased from CHARLES RIVER JAPAN, INC.) using heparin-containing syringes and stored under the frozen conditions in a freezer controlled at −30° C.

Experimental Results

Concentration-Dependency

Figure 2:
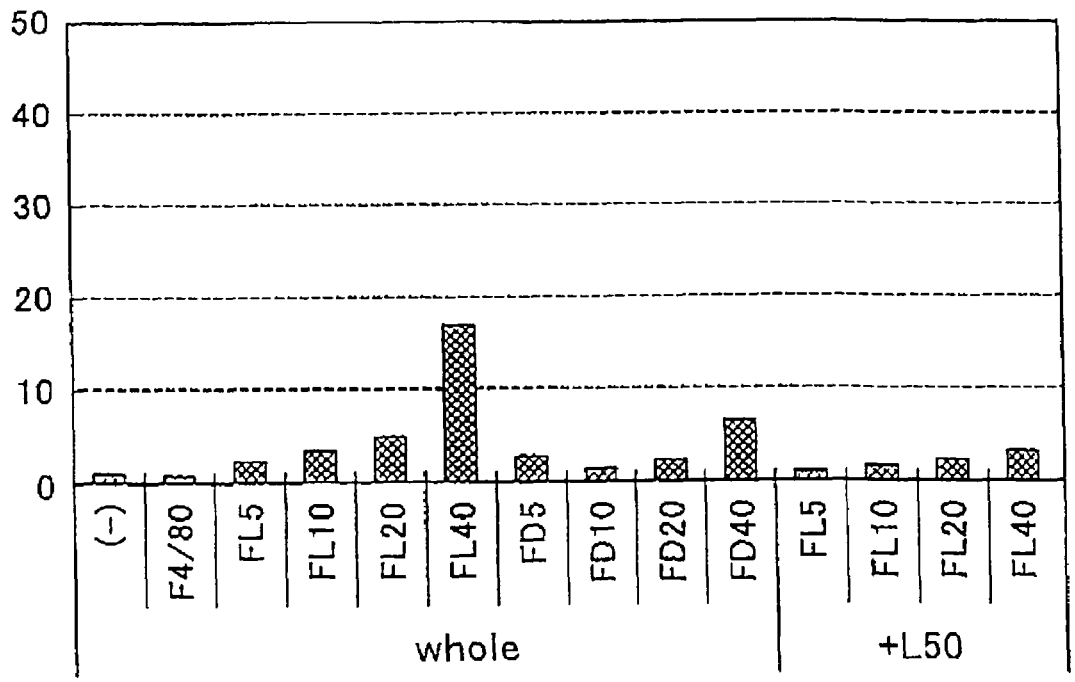
FIG. 2 shows the results of the fluorescein-labeled lentinan-binding to granulocytes tests, the FITC-labeled dextran-binding to granulocytes tests, and the binding to granulocytes test simultaneously using fluorescein-labeled lentinan and un-labeled lentinan.
Figure 3:
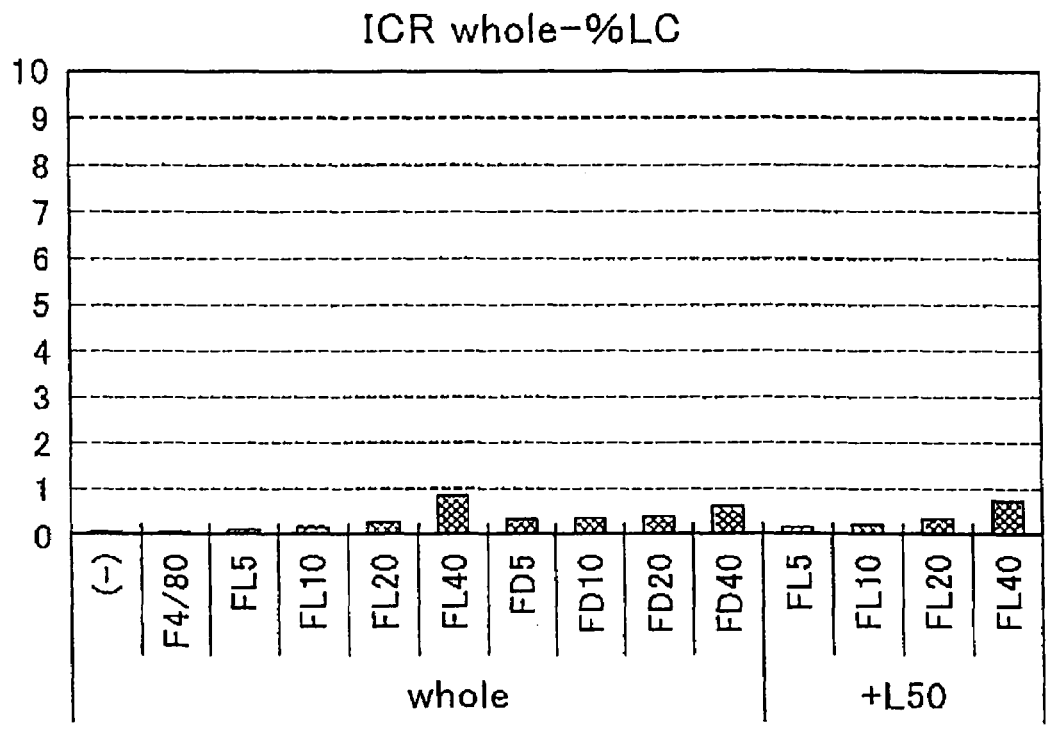
FIG. 3 shows the results of the fluorescein-labeled lentinan-binding to lymphocytes tests, those obtained in the FITC-labeled dextran-binding to lymphocytes tests, and the binding to lyphocytes test simultaneously using fluorescein-labeled lentinan and un-labeled lentinan.

The fluorescein-labeled lentinan was reacted with the whole blood of ICR mice for one hour at a final lentinan concentration of 5, 10, 20 or 40 μg/mL (FL5, FL10, FL20, FL40) and the cells bonded to the fluorescein-labeled lentinan were analyzed by FACS. The results thus obtained are plotted on FIGS. 1 to 3. Monocytes bound to fluorescein-labeled lentinan concentration-dependent and about 40% of the monocytes bound to the fluorescein-labeled lentinan at a fluorescein-labeled lentinan concentration of 40 μg/mL (see FIG. 1). There was likewise observed the fluorescein-labeled lentinan concentration-dependent binding ability of granulocytes and about 20% of granulocytes were bonded to the fluorescein-labeled lentinan (see FIG. 2) at a fluorescein-labeled lentinan concentration of 40 μg/mL. There was also observed the fluorescein-labeled lentinan concentration-dependent binding ability of lyphocytes, but the rate of linked cells was found to be only less than 1% even at a fluorescein-labeled lentinan concentration of 40 μg/mL (see FIG. 3).

Test on Binding-Inhibitory Effect of Lentinan

Using the whole blood of ICR mice, we tested the binding ability of blood cells. The addition of 50 μg/mL of the lentinan solution before the fluorescein-labeled lentinan was reacted for one hour at a final lentinan concentration of 5, 10, 20 or 40 μg/mL(FL5+L50, FL10+L50, FL20+L50, FL40+L50), inhibited the binding ability of cells to the fluorescein-labeled lentinan (see FIGS. 1 to 3).

Comparison with FITC-Labeled Dextran

The FITC-labeled dextran was reacted with the whole blood of ICR mice for one hour at a final dextran concentration of 5, 10, 20 or 40 μg/mL (FD5, FD10, FD20, FD40) and the cells bonded to the FITC-labeled dextran were analyzed by FACS. As a result, it was found that, for monocytes, there was not observed any linkage at an FITC-labeled dextran concentration of not more than 20 μg/mL, but about 5% of the cells were bonded to the dextran at a FITC-labeled dextran concentration of 40 μg/mL (see FIG. 1). Regarding granulocytes, there was not likewise observed any linkage, at an FITC-labeled dextran concentration of not more than 20 μg/mL, but about 10% of the cells were bonded to the dextran at a FITC-labeled dextran concentration of 40 μg/mL (see FIG. 2). In respect of lymphocytes, the rate of linked cells was found to be less than 1% (see FIG. 3).

Test Carried out Using Blood Stored in Frozen Conditions

Figure 4:
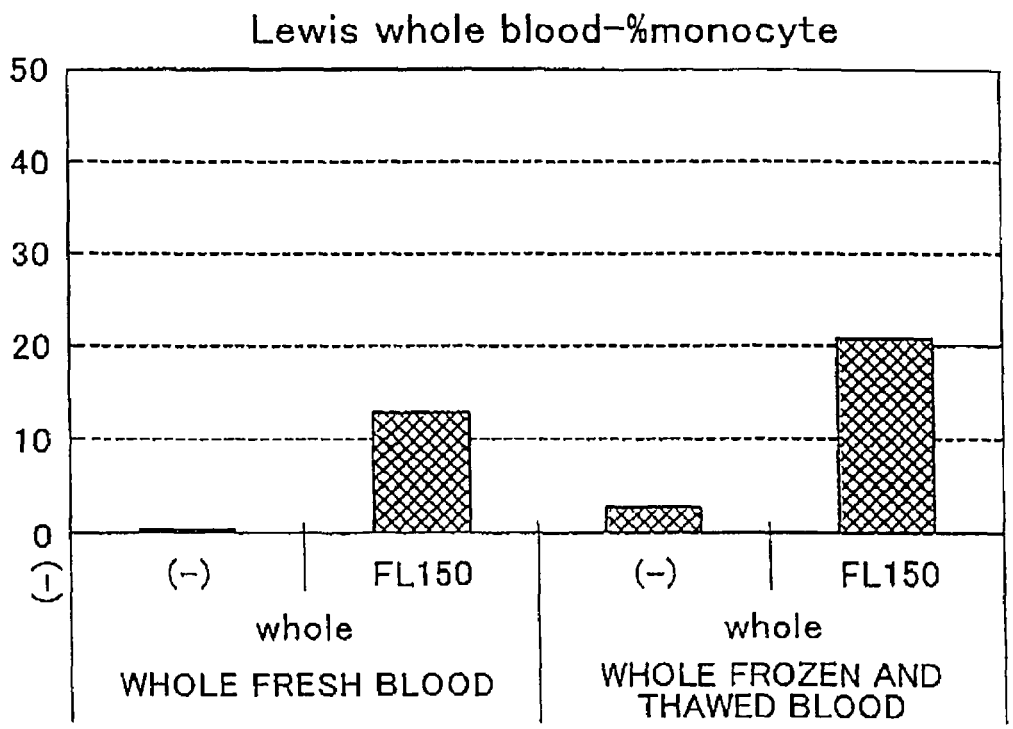
FIG. 4 shows the results of the fluorescein-labeled lentinan-binding tests of monocytes derived from a blood sample free of any freezing and thawing treatment and the frozen and thawed blood sample.

The fluorescein-labeled lentinan was reacted with the whole blood of rats which had been frozen and then thawed over one hour at a final fluorescein-labeled lentinan concentration of 150 μg/mL (FL150) and the cells bonded to the fluorescein-labeled lentinan were analyzed by FACS. As a result, it was found that there was observed almost the same binding rate observed for the blood which was free of any freezing and thawing treatment (see FIG. 4).

Conclusion:

For instance, the linked amount obtained by subtracting the amount (A1) of the FITC-labeled dextran bonded to the monocytes (MC) from that (B) of the fluorescein-labeled lentinan (FL) linked therewith is large as shown in FIG. 1. Accordingly, it may thus be predicted that lentinan is significantly bonded to the mouse's monocytes and that, in the light of this fact, lentinan would be effective as an immunostimulant agent for the mouse.

In addition, the linked amount obtained by subtracting the amount (A2) of the un-labeled lentinan and the fluorescein-labeled lentinan [FL+L50] bonded to the monocytes (MC) from that (B) of the fluorescein-labeled lentinan (FL) linked therewith is large as shown in FIG. 1. Accordingly, it may be confirmed that lentinan is specifically bonded to mouse monocytes and that monocytes are bonded to the fluorescein-labeled lentinan through the same manner of linkage observed for the linkage between the un-labeled lentinan and the monocytes of mice.

Example 2

Method for Determining Binding Ability Using Human Blood

The human blood collected using a heparin-containing blood-collection tube was dispensed into tubes in an amount of 250 μL/tube, while the same fluorescein-labeled lentinan used in Example 1 was likewise added to each tube such that the concentration thereof was equal to 100 μg/mL. After the cultivation thereof at 37° C. for 45 minutes, there was added, to each tube, a PE-labeled antibody against human CD14 (available from Caltag Company) and after the additional cultivation of the resulting mixture 37° C. for 30 minutes, there was added, to each tube, a 0.83% ammonium chloride solution (containing 0.1% sodium hydrogen carbonate and 0.0037% EDTA-4Na) in an amount of 10 mL/tube to thus carry out hemolysis. After the centrifugation of these tubes at 1500 rpm and room temperature for 5 minutes, the resulting residues were washed with a washing buffer (PBS(−)+0.2% BSA+0.1% sodium azide), suspended in 0.5 mL of the washing buffer, passed through a mesh and then subjected to the 2-color (fluorescein/PE) analysis using FACS Calibur.

We established gates for monocytes (MC), granulocytes (GC) and lymphocytes (LC) on the basis of forward and side scatter, and for analysis of monocytes, developed on Fluorescein/PE to thus determine the rate of the fluorescein-positive cells among the PE-positive cells, and for analysis of granulocytes and lymphocytes, determined the rate of the fluorescein-positive cells.

The similar analysis was carried out using FITC-labeled dextran (having a molecular weight of 2,000,000 available from Sigma Company) as a control (reference reagent 1) for the fluorescein-labeled lentinan. In this connection, the value obtained by subtracting the rate of the cells bonded to the FITC-labeled dextran from the rate of the cells bonded to the fluorescein-labeled lentinan is herein defined to be the rate of the cell which is positive to the lentinan-linkage (these results are plotted on FIGS. 5 and 6 and shown in FIG. 7 (indicated by FL)).

Furthermore, there were likewise investigated the blood samples stored at room temperature or in a refrigerator till the following day as well as the blood sample collected on a separate day.

Test on Binding-Inhibitory Effect of Lentinan

Figure 7:
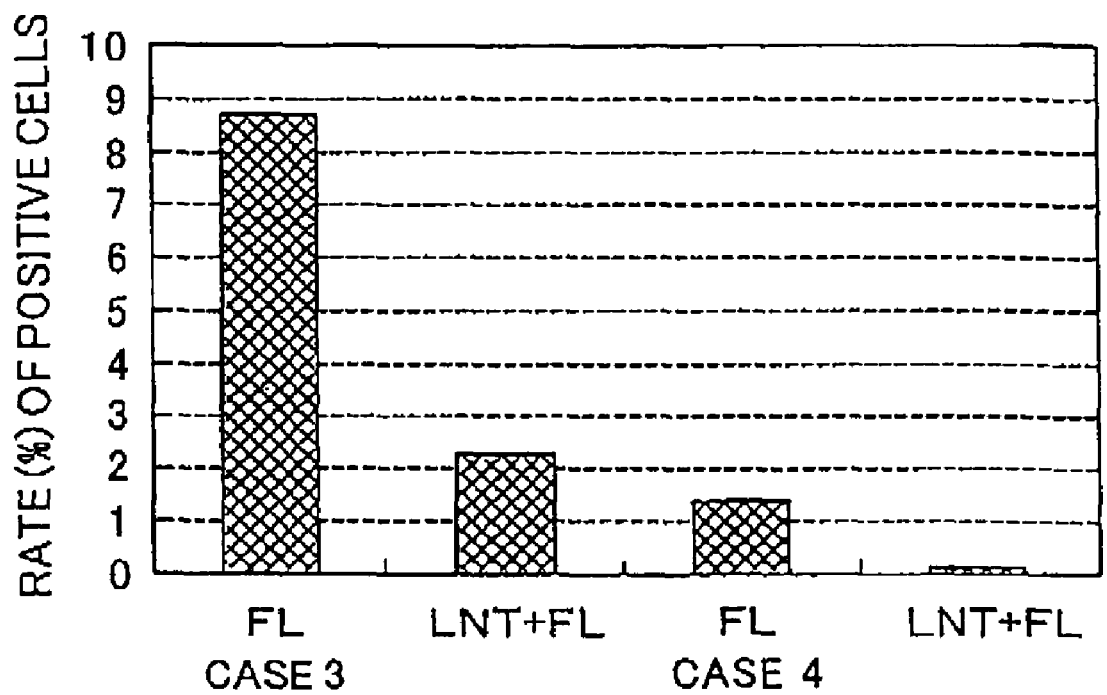
FIG. 7 shows the results of the binding-inhibitory tests of monocytes and under the coexistence of the fluorescein-labeled lentinan and un-labeled lentinan.

To the human blood sample, there was added the solution of lentinan (reference reagent 2) in a concentration of 100 μL/mL, the resulting mixture was cultured at 37° C. for 15 minutes, fluorescein-labeled lentinan was then added thereto in a concentration of 10 μg/mL and the resulting mixture was further cultivated at 37° C. for additional 30 minutes. Thereafter, a PE-labeled antibody (available from Caltag Company) against human CD14 was added thereto, the resulting mixture was cultured at 37° C. for 30 minutes, 2 mL/tube of FACS Lysing Solution (a hemolysis/fixation liquid available from BD Company; diluted 10 times with distilled water) and then the resulting mixture was allowed to stand at room temperature for 10 minutes for the hemolysis of the blood sample. The subsequent operations and analysis were carried out by repeating the same procedures used above in the binding ability-determining method (in the foregoing paragraph) (the results thus obtained are shown in FIG. 7 (indicated by LNT+FL)). The similar analysis was carried out using fluorescein-labeled dextran as a control (reference reagent 1) for the fluorescein-labeled lentinan.

Experimental Results

Method for Determining Binding Ability Using Human Blood

Figure 5:
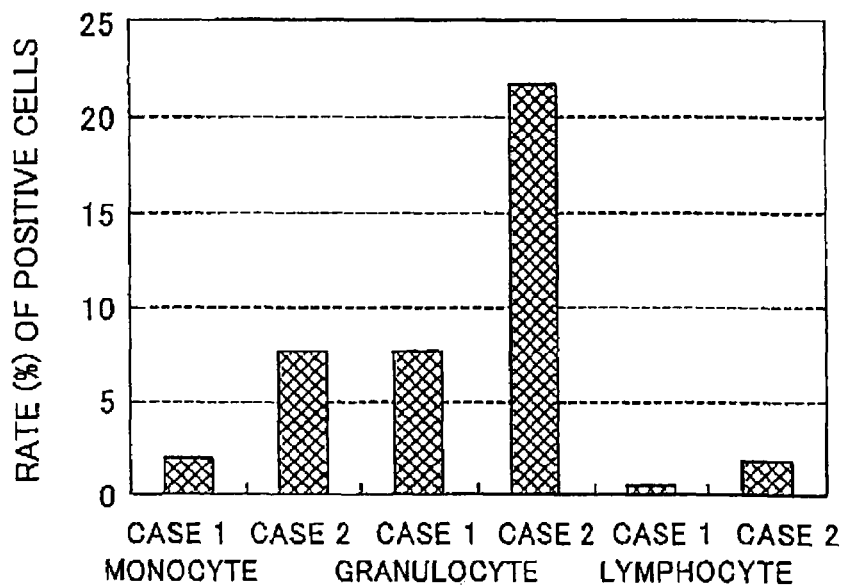
FIG. 5 shows the results of the fluorescein-labeled lentinan-binding tests of CD14-positive monocytes, granulocytes and lymphocytes.
Figure 6:
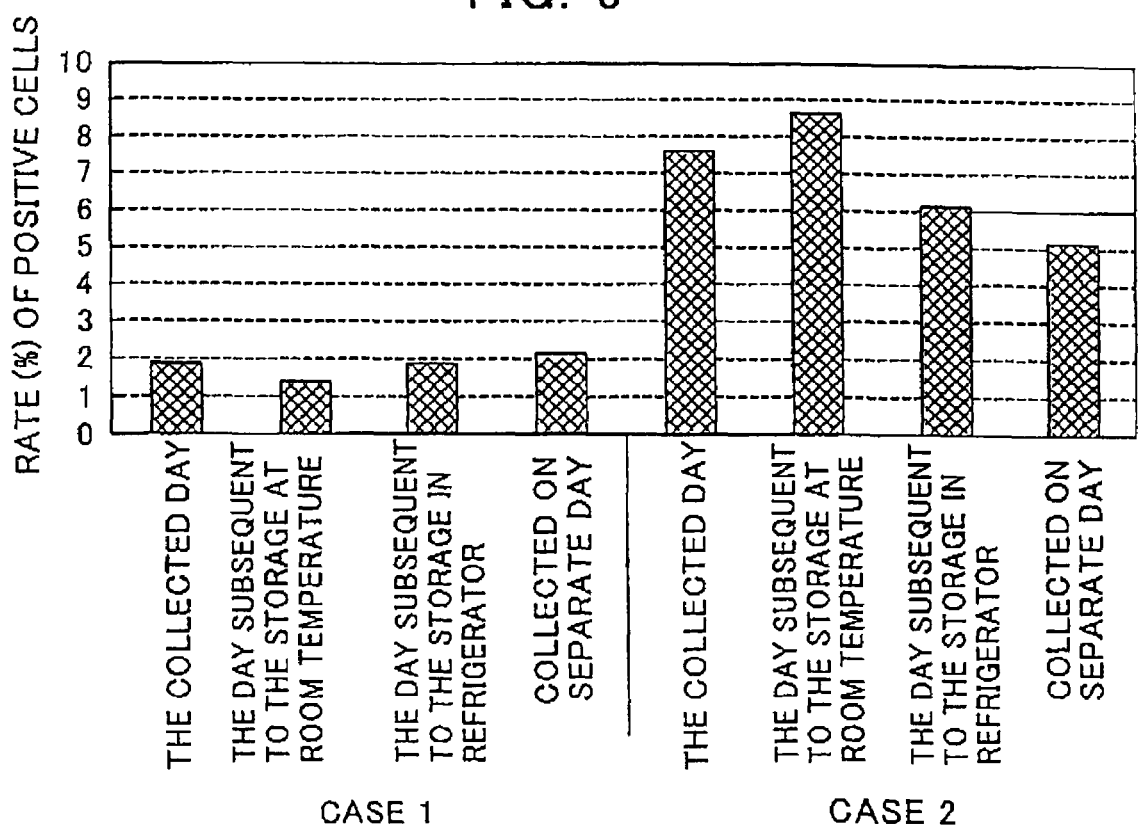
FIG. 6 shows the results of the fluorescein-labeled lentinan-binding tests of monocytes derived from the blood samples stored at room temperature or in a refrigerator till the day subsequent to their collection as well as the blood sample collected on a separate day.

The results obtained in two examples (Case 1 and Case 2) are plotted on FIGS. 5 and 6. There were observed individual differences in all of monocytes, granulocytes and lymphocytes, and the strength thereof was almost identical in either of the fraction (FIG. 5). Moreover, there were likewise investigated the blood samples stored at room temperature or in a refrigerator for one day as well as the blood sample collected on a separate day. The results observed for the both blood samples stored at room temperature and in a refrigerator were found to be identical to those observed on the day when the blood sample was collected. The same results were obtained even for the blood sample collected on separate day (see FIG. 6).

Test on Binding-Inhibitory Effect of Lentinan

The results observed for two experiments (Case 3 and Case 4) are plotted on FIG. 7. The data clearly indicate that the binding of the fluorescein-labeled lentinan with cells was inhibited by addition of 100 μg/mL lentinan solution before 10 μg/mL fluorescein-labeled lentinan was reacted Conclusion:

For instance, as shown in FIGS. 5 and 7, the linked amount (specified in the figure) obtained by subtracting the amount (A1) of the FITC-labeled dextran bonded to monocytes (MC) from that (B) of the fluorescein-labeled lentinan (FL) linked therewith is large. Accordingly, it may thus be predicted that lentinan is bonded to human monocytes in Case 1, Case 2, Case 3 and Case 4 and that, in the light of the magnitudes of the linked amounts, lentinan would be more effective as an immunostimulant agent for men in Case 2 and Case 3.

In addition, as shown in FIG. 7, the linked amount obtained by subtracting the amount (A2) of the un-labeled lentinan and the fluorescein-labeled lentinan [LNT+FL] bonded to monocytes (MC) from that (B) of the fluorescein-labeled lentinan (FL) linked therewith is large. Accordingly, it may be assumed that lentinan is specifically bonded to human monocytes in Case 3 and Case 4 and that, in the light of the magnitudes of the linked amounts, lentinan would be more effective as an immunostimulant agent for men in Case 3.

Furthermore, as shown in FIG. 6, almost the same results obtained above were observed even when using the blood samples stored at room temperature and in a refrigerator for one day as well as the blood sample collected on some other day. This clearly indicates that the use of the kit of the present invention would permit the stable determination of the binding ability of polysaccharides and the more precise measurement of the binding ability of polysaccharides peculiar to each particular subject to be examined.

Example 3

Investigation of Dependency on Difference in Mouse Strain

The blood samples were collected through the hearts of ICR mice (4 to 6-week-old female mice purchased from CLEA Japan, Inc.), a BALB/c mouse (11 to 13-week-old female mice purchased from CHARLES RIVER JAPAN INC.), a C57BL/6 mouse (10 to 11-week-old male mice purchased from CLEA Japan, Inc.), a C3H/HeN mouse, C3H/HeJ mouse (6 to 8-week-old female mice purchased from CLEA Japan, Inc.) under the anesthetization with ether using heparin-containing syringes. The measurement was carried out three times for each mouse. Each heparin-treated blood sample was dispensed into Falcon 2054 tubes in an amount of 90 μL/tube under ice-cooled conditions and the fluorescein-labeled lentinan was likewise dispensed into these tubes in an amount of 10 μL/tube. After the elapse of not less than 30 minutes, there was added, to each tube, 3 μL/tube of a PE-labeled antibody against the surface antigen F4/80 of the mouse monocyte (PE-labeled anti-mouse F4/80 antibody available from Serotec Company). Further, after the elapse of an additional time on the order of not less than 30 minutes, there was added, to each tube, 3 mL/tube of FACS Lysing Solution (a hemolysis/fixation liquid available from BD Company; diluted 10 times with distilled water) and then the resulting mixture was allowed to stand at room temperature for 10 minutes for the hemolysis of the blood sample. After the centrifugation at 1500 rpm and 4° C. for 5 minutes, the resulting residues were washed with 1 mL of a washing buffer (PBS(−)+0.1% BSA+0.1% sodium azide) (washing/analysis liquid), suspended in 0.5 mL of the washing buffer, passed through a mesh and then subjected to the 2-color (fluorescein/PE) analysis using FACS Calibur.

We established gates for monocytes (MC), granulocytes (GC) and lymphocytes (LC) on the basis of forward and side scatter, and for analysis of monocytes, developed on Fluorescein/PE to thus determine the rate of the fluorescein-positive cells among the PE-positive cells.

The similar analysis was carried out using FITC-labeled dextran (having a molecular weight of 2,000,000 available from Sigma Company) as a control (reference reagent 1) for the fluorescein-labeled lentinan.

Experimental Results

Investigation of Dependency on Difference in Mouse Strain

Figure 8:
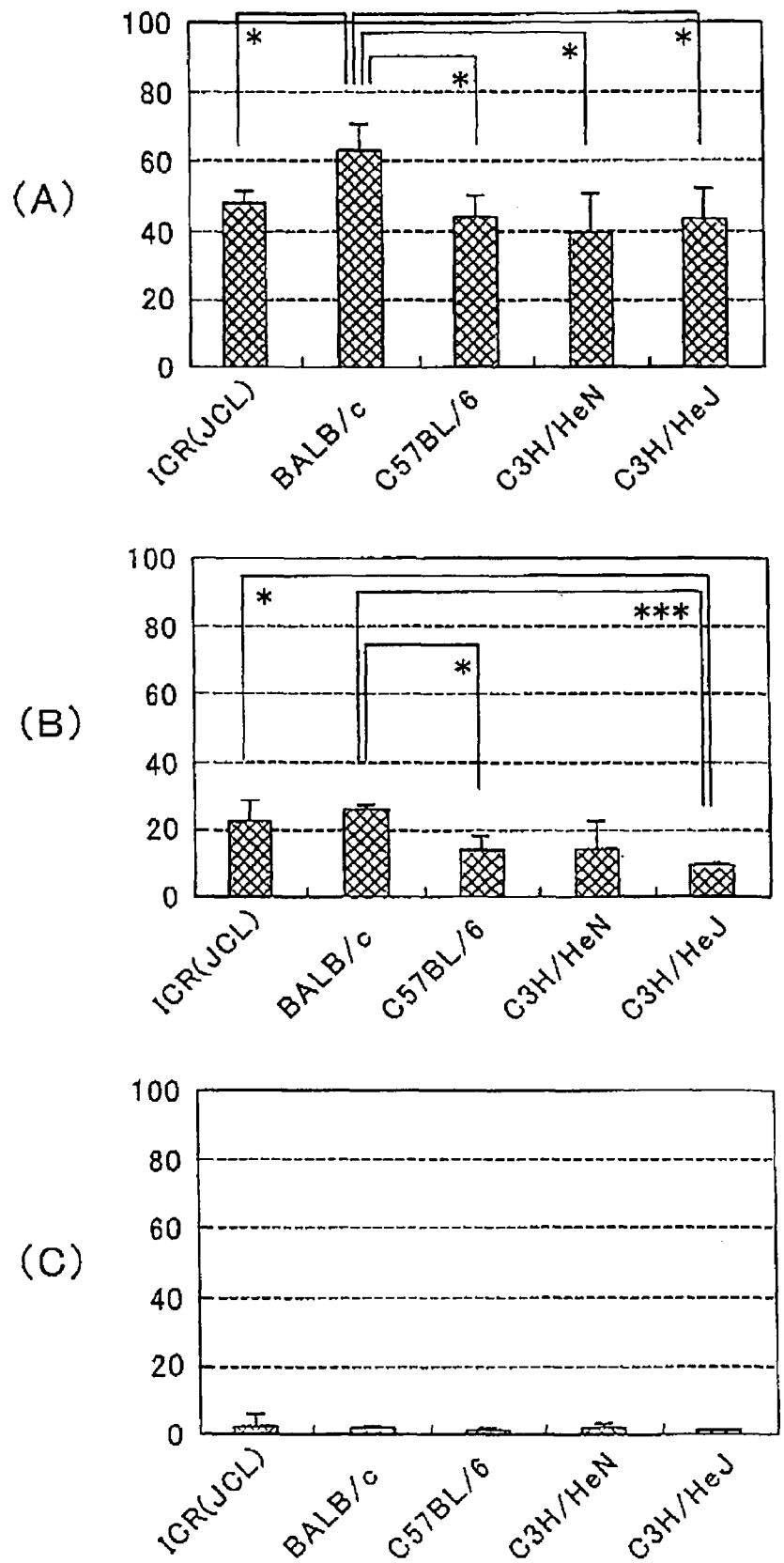
FIG. 8 shows the results of the fluorescein-labeled lentinan-binding tests and the FITC-labeled dextran-binding tests of F4/80-positive monocytes. In this figure.

FIG. 8 shows average values of the rate of the fluorescein-positive cells among the F4/80-positive monocytes. When monocytes were reacted with 20 μg/mL of the fluorescein-labeled lentinan, there were observed almost the same results for the mouse strains examined except that the BALB/c mouse showed a higher rate (see FIG. 8A). When monocytes were reacted with 5 μg/mL of the fluorescein-labeled lentinan, the rates were as follows (in a descending order): BALB/c≧ICR>C57BL/6≈C3H/HeN≧C3H/HeJ (see FIG. 8B). In addition, when monocytes were reacted with 20 μg/mL of the FITC-labeled dextran, there was not observed any linkage between them (see FIG. 8C).

CONCLUSION

For instance, as shown in FIG. 8B, there were observed higher rates of linkage in cases of BALB/c mice and ICR mice, while C3H mice showed low rates of linkage and it would be predicted that lentinan is highly effective as an immunostimulant agent for BALB/c and ICR mice while it is less effective for C3H mice.

Contrary to this, in Non-Patent Document Nos. 1 and 6, there are disclosed results obtained by subcutaneously transplanting S180 mouse sarcoma cells to various mice different in strains and then investigating anti-tumor effects of lentinan. According to this investigation, lentinan exerts higher anti-tumor effects on the models of ICR and BALB/c mice to which S180 sarcoma cells have been subcutaneously transplanted, medium anti-tumor effects on the tumor models obtained using C57BL/6 mice, and weak anti-tumor effects on the tumor models obtained using C3H mice. This tendency was found to be identical to that observed for the strength of the rates of linkages formed between the cells and the fluorescein-labeled lentinan.

This clearly indicates that the determination of the specific binding ability of a target immunostimulant polysaccharide would certainly permit the estimation of the effectiveness of the target immunostimulant polysaccharide as an immunostimulant agent (Int. J. Immunotherapy, 1980, 5(4):145).

What is claimed is:

1. A kit for determining the activity of a peripheral blood mononuclear cell to bind to a polysaccharide, which comprises a detection reagent comprising a fluorescence-labeled immunostimulant polysaccharide; and a reference reagent,
   wherein said reference reagent comprises a fluorescence-labeled material of a polysaccharide which is different from that in the fluorescence-labeled immunostimulant polysaccharide present in the detection reagent.

2. The kit of claim 1, wherein the immunostimulant polysaceharide is a β-glucan.

3. The kit of claim 1, wherein the immunostimulant polysaccharide is lentinan.

4. The kit of claim 1, wherein the detection reagent and the reference reagent are liquid, respectively and contained in separate containers.

5. The kit of claim 4, wherein said immunostimulant polysaccharide is a member selected from the group consisting of a β-glucan, an α-glucan, a hetero-glucan, and a protein-bound glucan.

6. The kit of claim 4, wherein said immunostimulant polysaccharide is a β-glucan.

7. The kit of claim 4, wherein said immunostimulant polysaccharide is a β-glucan selected from the group consisting of lentinan, zymosan, pachymaran, schizophyllan, pustulan, scleroglucan, and lichenan.

8. The kit of claim 4, which further comprises a hemolysis/fixation liquid.

9. The kit of claim 8, wherein said immunostimulant polysaccharide is a member selected from the group consisting of a β-glucan, an α-glucan, a hetero-glucan, and a protein-bound glucan.

10. The kit of claim 8, wherein said immunostimulant polysaccharide is a β-glucan.

11. The kit of claim 8, wherein said immunostimulant polysaccharide is a β-glucan selected from the group consisting of lentinan, zymosan, pachymaran, schizophyllan, pustulan, scieroglucan, and lichenan.

12. The kit of claim 8, which further comprises a washing/analysis liquid.

13. The kit of claim 12, wherein said immunostimulant polysaccharide is a member selected from the group consisting of a β-glucan, an α-glucan, a hetero-glucan, and a protein-bound glucan.

14. The kit of claim 12 wherein said immunostimulant polysaccharide is aβ-glucan.

15. The kit of claim 12, wherein said immunostimulant polysaccharide is a β-glucan selected from the group consisting of lentinan, zymosan, pachymaran, schizophyllan, pustulan, scleroglucan, and lichenan.

16. The kit of claim 1, wherein the reference reagent further comprises an immunostimulant polysaccharide which is not labeled with any fluorescent material and whose polysaccharide moiety is identical to that in the fluorescence-labeled immunostimulant polysaccharide in the detection reagent.

17. The kit of claim 1, which further comprises a blood-collection tube.

18. The kit of claim 1, wherein said immunostimulant polysaccharide is a member selected from the group consisting of a β-glucan, an α-glucan, a hetero-glucan, and a protein-bound glucan.

19. The kit of claim 1, wherein said immunostimulant polysaccharide is a β-glucan selected from the group consisting of lentinan, zymosan, pachymaran, schizophyllan, pustulan, scieroglucan, and lichenan.

* * * * *